US00PP11066P

United States Patent [19]

Lowe et al.

[11] Patent Number: Plant 11,066

[45] Date of Patent: Sep. 21, 1999

[54] KIWI PLANT NAMED 'HORT16A'

[76] Inventors: Russell G Lowe, The Horticulture and Food Research Institute of N.Z. Ltd, Private Bag 11030; Hinga D Marsh; Mark A McNeilage, both of The Horticulture and Food Research Institute of New Zealand Limited, Private Bag 11030, all of Palmerston North, New Zealand

[21] Appl. No.: 08/996,829

[22] Filed: Dec. 23, 1997

[51] Int. Cl.[6] ..... A01H 5/00

[52] U.S. Cl. ..... Plt./156

[58] Field of Search ..... Plt./33.1, 156

*Primary Examiner*—Howard J. Locker
*Assistant Examiner*—Melissa L. Kimball
*Attorney, Agent, or Firm*—Quarles & Brady

[57] ABSTRACT

A new and distinct kiwi plant of the species *Actinidia chinensis* Planch. is described. The cultivar results from a controlled pollination using a male *A. chinensis* selection CK15_01 of unknown parentage, and a female *A. chinensis* selection CK01_01_01_01. Both named parents (CK15_01 and CK01_01_01_01) are unpatented cultivars. The new cultivar is distinguished by its short silky hair, protruding stylar end, golden flesh and sweet tropical taste.

4 Drawing Sheets

BACKGROUND TO THE INVENTION

Kiwi plants in cultivation are deciduous vines of *A.deliciosa*. There are more than 50 species in the genus Actinidia originating in China and parts of Asia. The kiwi cultivar 'Hayward', developed in New Zealand, is the most widely grown cultivar because of its distinctive green flesh, good flavor and long storage life.

Less well known outside of mainland China is the species *A. chinensis,* closely related to *A. deliciosa*. Fruit can be as large as the kiwi, generally have much finer, softer hairs on the fruit skin, and can have either green or yellow flesh. Many Chinese prefer fruit of *A. chinensis* rather than the kiwi of commerce, considering the flavor to be superior. Like the kiwi, plants are dioecious, so male pollinizers are required as well as female plants to ensure fruit production.

*A. chinensis* plants grow vigorously in spring, and rapidly develop canes up to 4 m long if not managed correctly. Plants require a mild, warm-temperate climate, free from spring and early autumn frosts, and need well-drained soils to produce consistent heavy crops. Regular irrigation is necessary in dry spells. *A. chinensis* flowers in spring (mid-October to mid-November) in New Zealand. Harvest of *A. chinensis* fruit may occur between April and mid-May in New Zealand, depending on the selection and location of plantings.

SUMMARY OF THE INVENTION

The present invention relates to a new and distinctive kiwi plant having a generally ovoid shaped fruit which tapers towards the stylar end and which has soft, silky hair. More particularly, the new cultivar is designated 'Hort16A' and is derived from a controlled pollination of *A. chinensis* CK15_01, a male selection of unknown parentage, and *A. chinensis* female CK01_01_01. Both parents were derived from seedling plants grown from two introductions of seeds from China in 1981 and 1978 and are unpatented.

The new cultivar of kiwi was created in the course of a plant breeding program which was initiated during 1987 at Hort Research in Auckland, New Zealand. The cross made by Mark McNeilage in November 1987. Seed were sown in winter 1988 and 312 seedlings from this cross were planted out in the field at Te Puke Research Centre in spring,1988. The seedlings first fruited in May 1990 and 'Hort16A' (breeding code CK01_02_01_01) was selected, after storage and sensory evaluation in 1991 and 1992 by Russell Lowe and Hinga Marsh.

The new cultivar can be asexually reproduced as cuttings or by grafting or budding on to seedling or cutting-grown rootstocks of *A. deliciosa* or *A. chinenis.* Trial plantings on seedling rootstocks, established in 1992 at Te Puke, have shown that the unique combination of characteristics come true to form and are established and transmitted through succeeding asexual propagations.

'Hort16A' flowers four weeks ahead of the unpatented 'Hayward' variety, so the usual pollinizers used for 'Hayward' are ineffective as well as being of a different species and ploidy. Two new and unpatented early-flowering *A. chinensis* male pollinizers, designated Hortkiwi 'Meteor' and Hortkiwi 'Sparkler', have been selected as males for use in new plantings of 'Hort16A'.

BRIEF DESCRIPTION OF THE ILLUSTRATIONS

Figure 1:
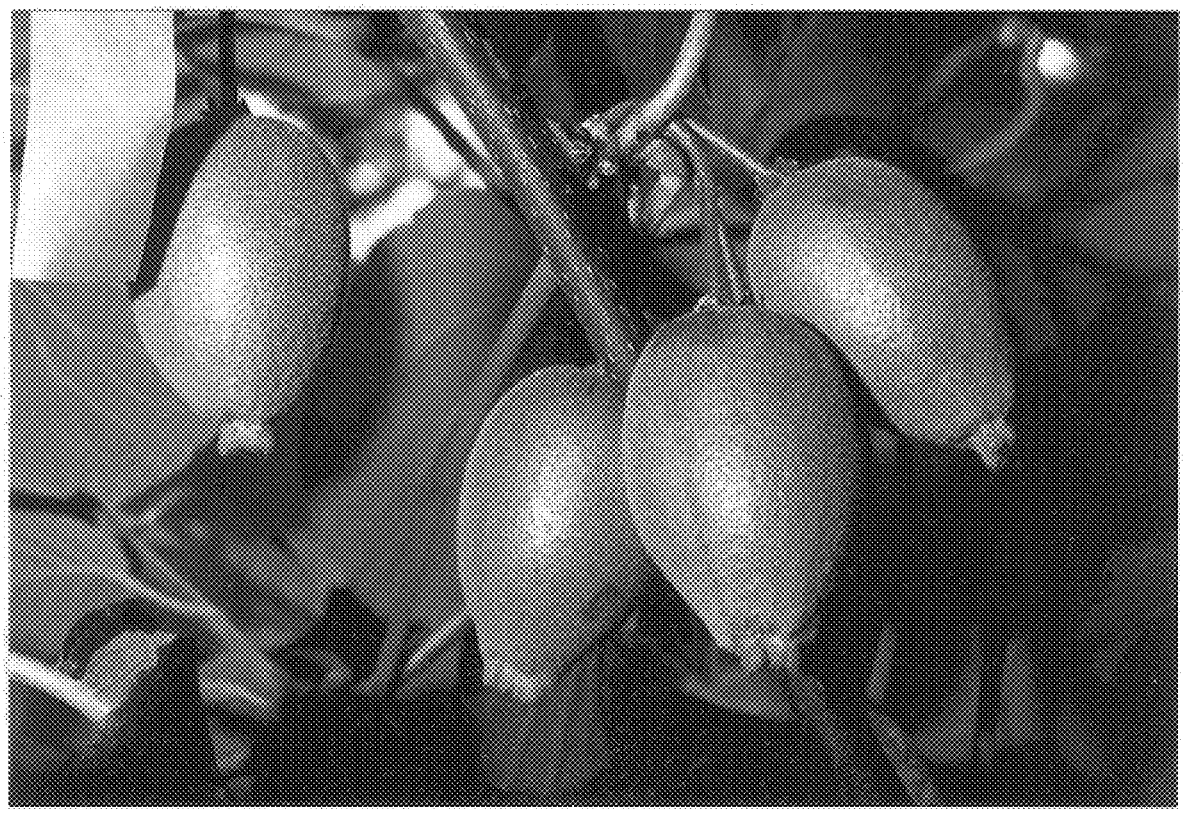
FIG. 1 shows typical fruit of the cultivar 'Hort16A' on the vine
Figure 2:
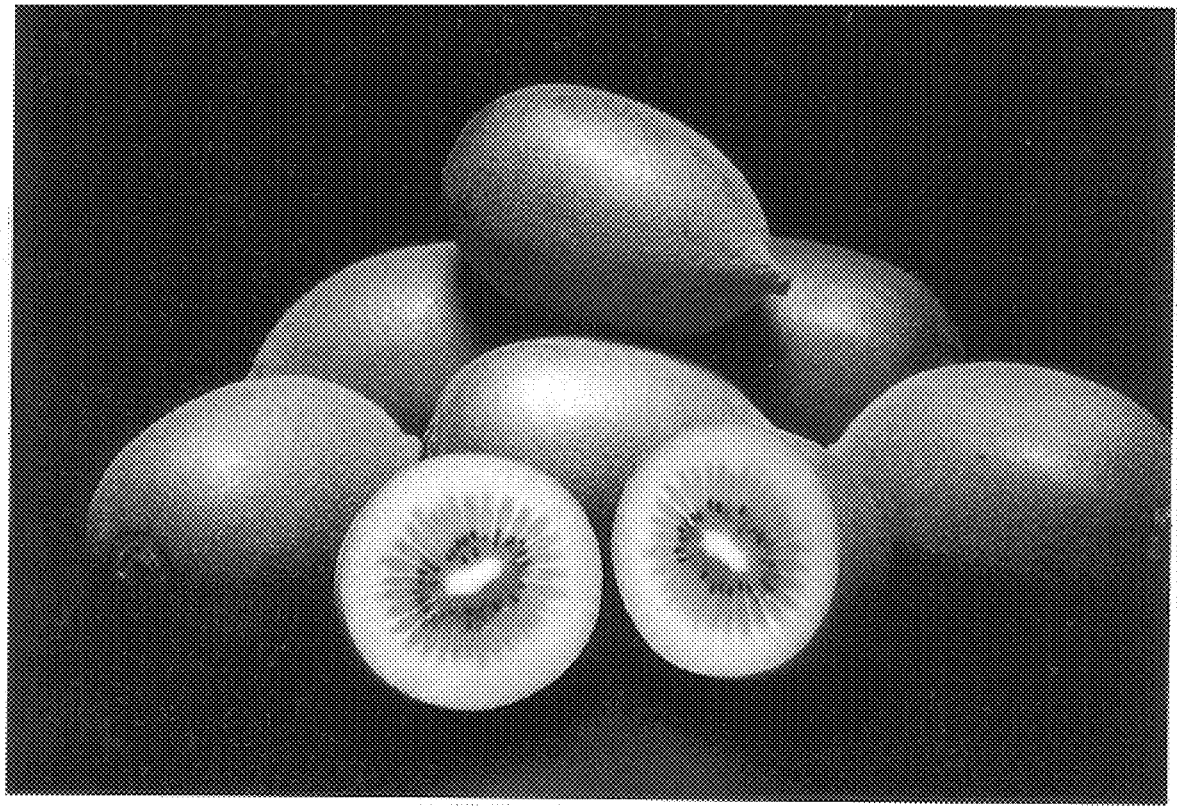
FIG. 2 shows typical fruit of the cultivar 'Hort16A'
Figure 3:
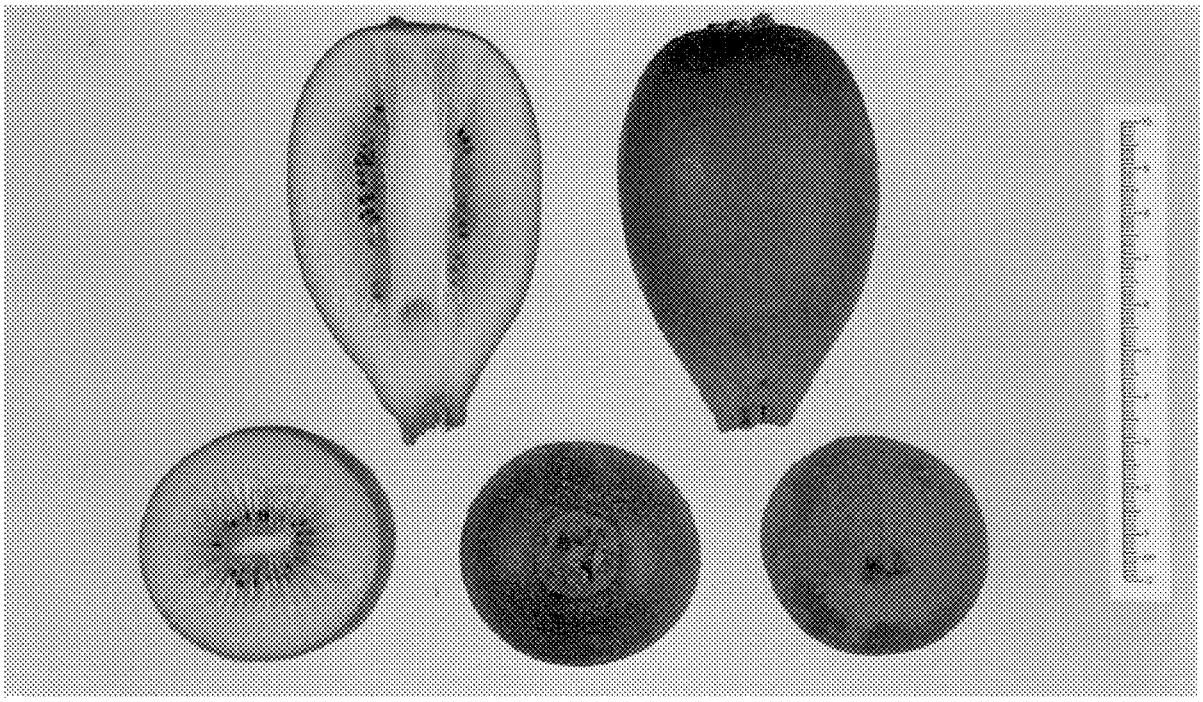
FIG. 3 shows 'Hort16A' fruit in cross-section and profile
Figure 4:
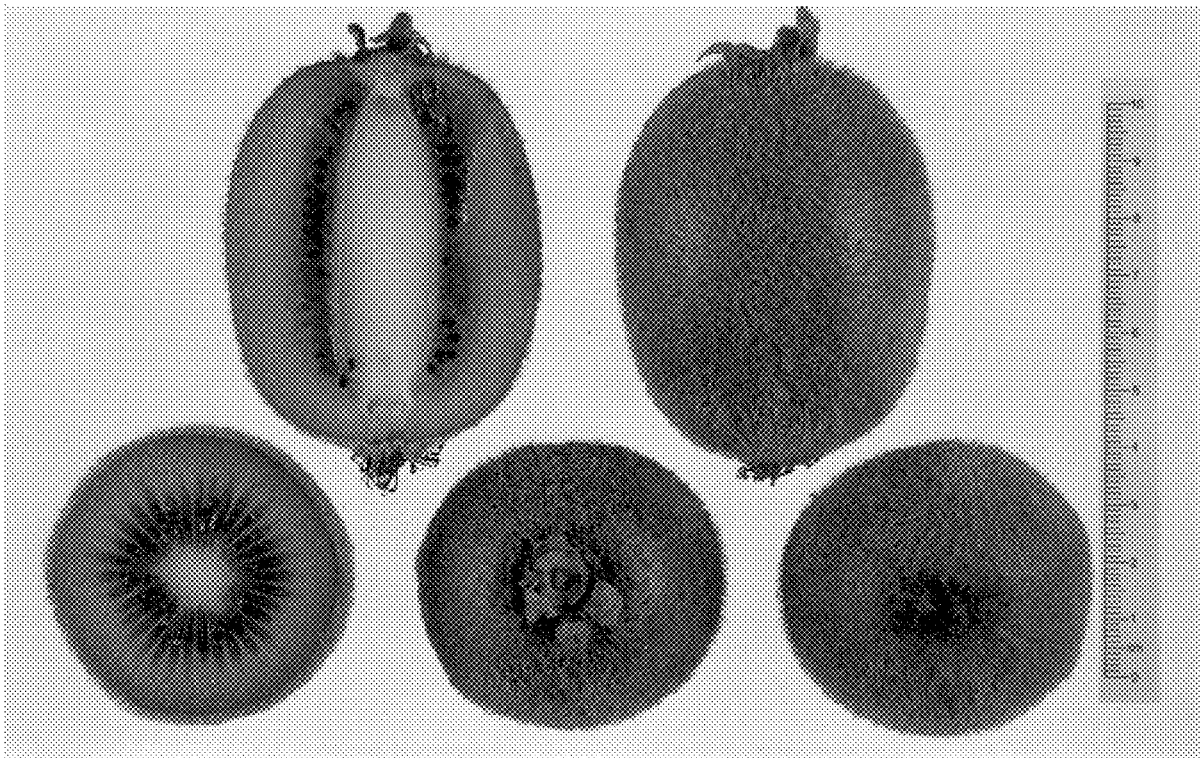
FIG. 4 shows 'Hayward' fruit in cross-section and profile
Figure 5:
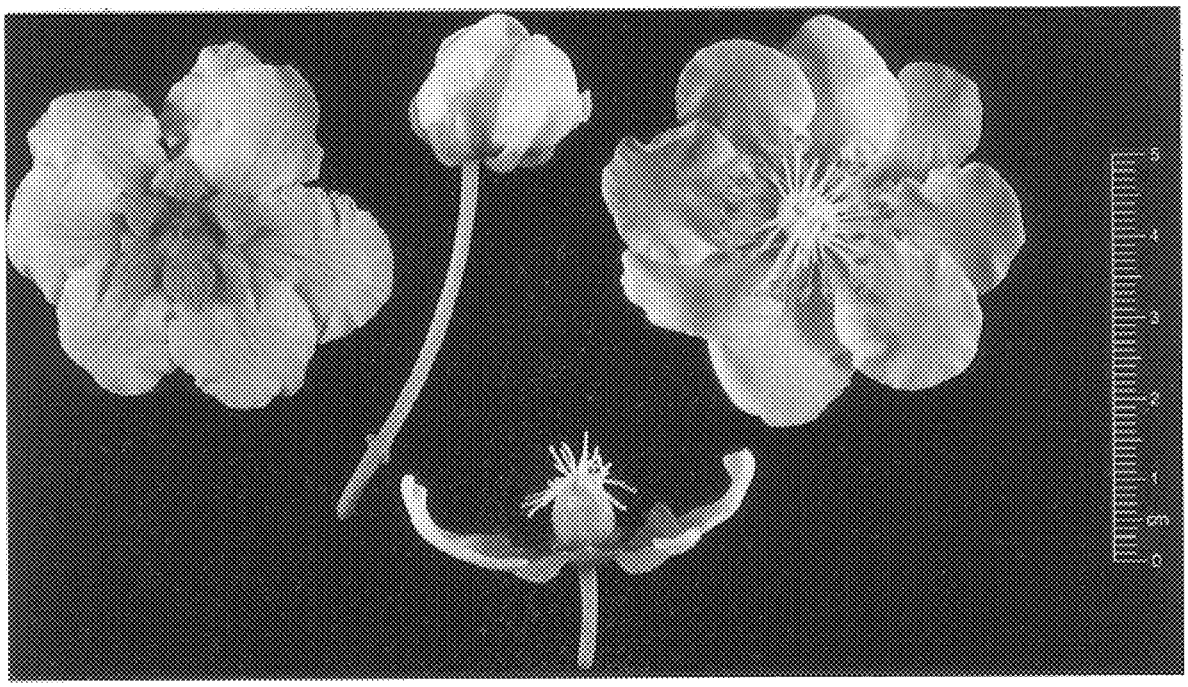
FIG. 5 shows flowers of the cultivar 'Hort16A'
Figure 6:
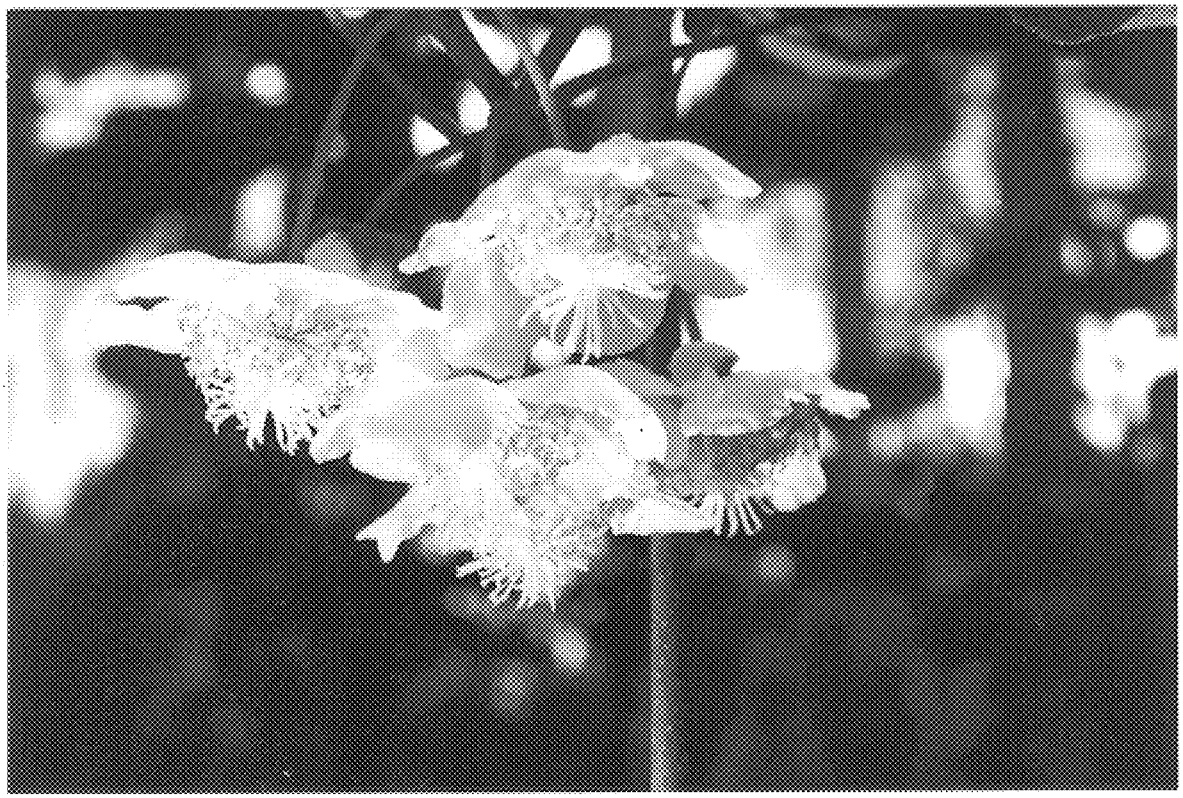
FIG. 6 shows flowers of the cultivar 'Hayward'
Figure 7:
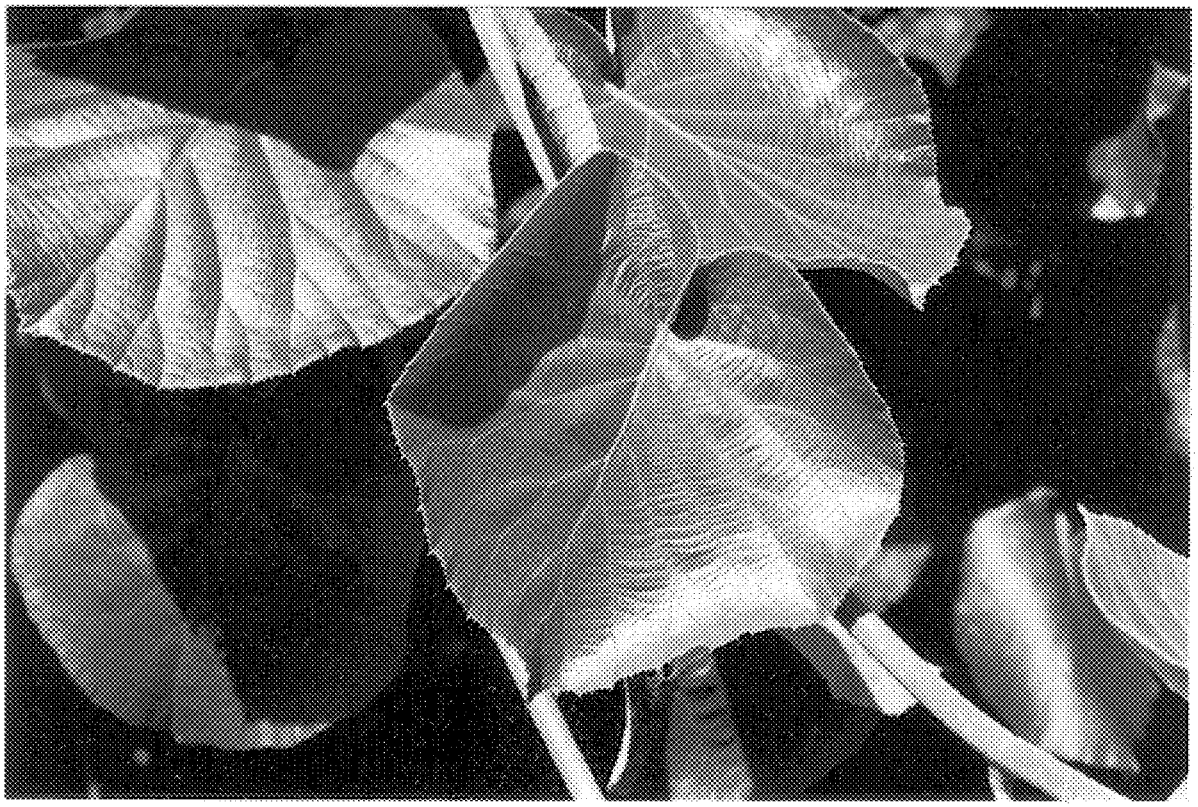
FIG. 7 shows mature leaves of 'Hort16A'
Figure 8:
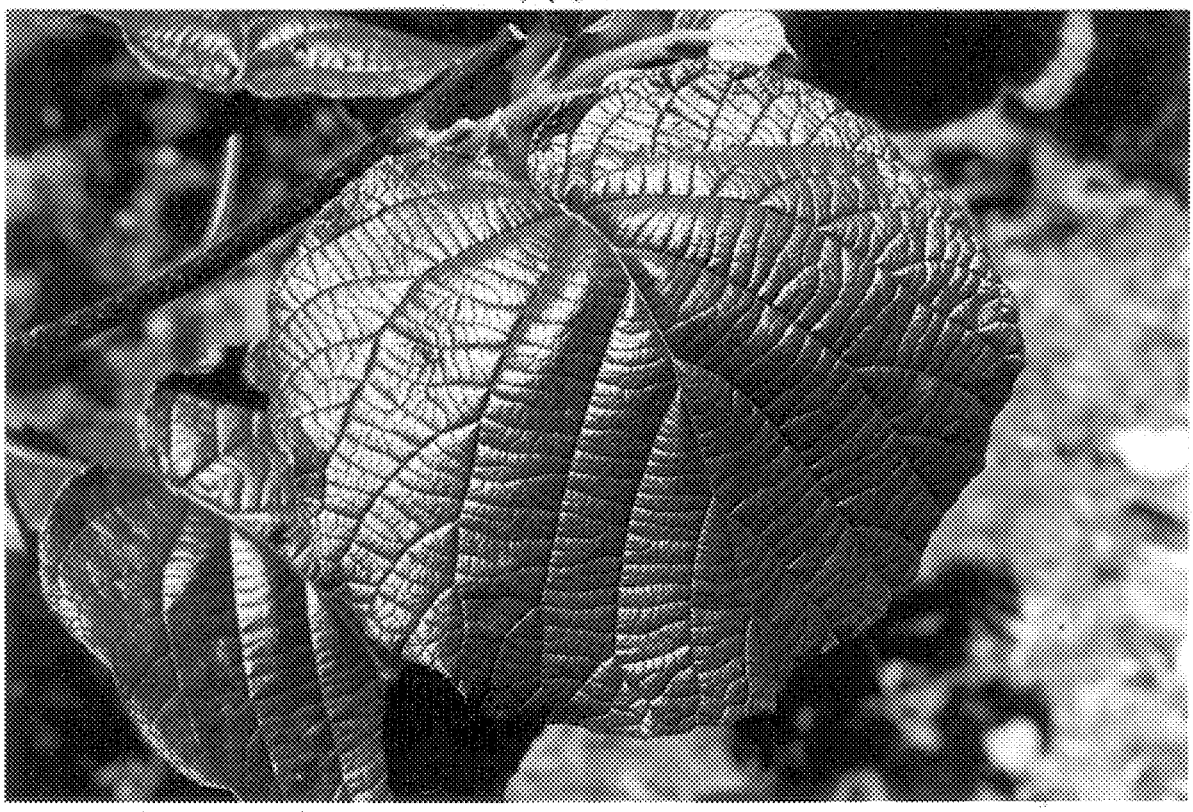
FIG. 8 shows a mature leaf of 'Hayward'

Photographs of fruit were taken after the normal harvest date. Colors may vary depending upon growing conditions under different climate, soil, and cultivation conditions and the fruit skin color may vary depending upon extent of exposure to direct sunlight.

COMPARISON TO CLOSEST CULTIVAR

The distinctive characteristics of this new kiwi cultivar, described in detail below, were observed in 1994 at Te Puke, New Zealand. The age of the plants was 3 years from the graft. Comparison 'Hayward' vines were grown in another block on the same orchard.

The fruit of 'Hort16A' is ovoid in shape and has a protruding distal end unlike 'Hayward' which has a rounded distal end. 'Hort16A' fruit are generally circular in cross-section although slightly flattened. 'Hort16A' fruit has a much smaller core than 'Hayward' and the flesh of ripe fruit is golden yellow whereas 'Hayward' flesh is green. The hairs on the skin of the fruit of 'Hort16A' are much finer, soft to the touch, and are very easily removed by rubbing or brushing to reveal a leathery, almost shiny skin. The skin color of 'Hort16A' fruit is a yellow-brown in contrast to that of 'Hayward' which is a medium brown color. 'Hort16A' fruit have a higher dry matter content at harvest and are much sweeter tasting than 'Hayward' fruit when ripe. While 'Hort16A' fruit soften more rapidly than 'Hayward' in coolstorage, fruit will stay at about 1 kg firmness for up to 3 months without further significant softening.

BOTANICAL DESCRIPTION OF THE PLANT

The new cultivar 'Hort16A' is pistillate, with imperfect flowers, i.e. the flowers produce only sterile pollen and thus require a pollinizer for fruit production. Two specific *A. chinensis* pollinizers, named Hortkiwi 'Meteor' and Hortkiwi 'Sparkler', have been developed for 'Hort16A'. Characteristics of the new cultivar, in which it differs from the standard kiwi cultivar 'Hayward', include earlier flowering time, protruding stylar end on the fruit, silky easily-removed hairs on the skin, golden flesh when ripe, and yellow-brown colored skin.

TABLE OF CHARACTERISTICS

Horticultural terminology is used in accordance with revised UPOV guidelines for kiwi.

Characters of comparison cultivar 'Hayward' are noted opposite that character in [brackets] when significantly different.

'Hayward' plants were observed in a planting on the same orchard, but not the same plot.

All dimensions in millimeters unless otherwise stated, weights in grams.

| | Hort16A | Hayward |
|---|---|---|
| PLANT | | |
| Plant: sex expression | female (flowers imperfect) | |
| Plant: ploidy | diploid (2n = 2x = 58) | [hexaploid] |
| Plant: vigor | strong | [medium] |
| Young shoot: hairs | present | |
| Young shoot: density of hairs | medium | |
| Young shoot: type of hairs | short | [hirsute] |
| Young shoot: anthocyanin coloration of growing tip | absent | [medium] |
| Young shoot: anthocyanin coloration of leaf axil | absent | |
| STEM | | |
| Stem: coloration of leaf axil | absent | [weak] |
| Stem: diameter | medium - Mean 11.0 mm (Range 8.3–13.3 mm) | |
| Stem: dormant bud diameter | 6.9 mm (4.9–8.3 mm) | |
| Stem: color on upper side of shoot | dark-brown | |
| Stem: character of bark | smooth | [medium] |
| Stem: hairs | present | |
| Stem: conspicuousness of lenticels | conspicuous | |
| Stem: number of lenticels | medium | |
| Stem: color of lenticels | brownish-white | [greyish-white] |
| Stem: size of bud support | medium | |
| Stem: visibility of bud (dormant canes) | visible | [almost buried] |

-continued

TABLE OF CHARACTERISTICS

Horticultural terminology is used in accordance with revised UPOV guidelines for kiwi.

Characters of comparison cultivar 'Hayward' are noted opposite that character in [brackets] when significantly different.

'Hayward' plants were observed in a planting on the same orchard, but not the same plot.

All dimensions in millimeters unless otherwise stated, weights in grams.

| | Hort16A | Hayward |
|---|---|---|
| Stem: number of hairs visible on bud (dormant canes) | medium | |
| Stem: leaf scar | medium | |
| LEAF (Mature) | | |
| Leaf: general shape of blade | very broadly ovate | |
| Leaf: length | 170.3 mm (145–198 mm) | |
| Leaf: width | 186.3 mm (159–217 mm) | |
| Leaf: petiole length | 166.8 mm (100–250 mm) | |
| Leaf: shape of tip of blade | cuspidate | [mucronate] |
| Leaf: shape of base of blade | cordate | |
| Leaf: arrangement of leaf bases | overlapping | |
| Leaf: puckering/blistering on upper side of blade | weak | [medium] |
| Leaf: margin | ciliate | |
| Leaf: green color of upper side of blade | light-medium | |
| Leaf: glossiness of upper surface of blade | medium | |
| Leaf: color of lower side of blade | light green | |
| Leaf: glaucosity (lower side of blade) | absent | |
| Leaf: hairs on petiole | present | |
| Leaf: density of hairs on petiole | medium | |
| Leaf: anthocyanin coloration on upper side of petiole | medium | |
| FLOWER | | |
| (Measurements are from a 20 flower sample) | | |
| Inflorescence: predominant number of flowers | one | |
| Pedicel: length | medium - 42.0 mm (29.9–49.20 mm) | |
| Pedicel: hairs | present | |
| Pedicel: length of hairs | very short | |
| Flower: number of sepals | >5 | |
| Flower: color of sepals | pale green | |
| Flower: diameter (terminal or king flower when fully open) | large - 47.9 mm (42.3–52.5 mm) | |
| Flower: petal length | 23.1 mm (20.8–25.4 mm) | |
| Flower: petal width | 17.7 mm (15.8–19.1 mm) | |
| Flower: petal length/width ratio | 1.31 mm (1.14–1.45 mm) | |
| Flower: mean number of petals per flower | 8 (6–10) | |
| Flower: number of flowers with more than six petals | 17 out of 20 flowers | |
| Flower: arrangement of petals | overlapping | |
| Flower: petal shoulder | present | |
| Flower: primary color of petals (when fully open) | white | |
| Flower: type of coloration of petals | uniform color over whole petal | |
| Flower: style number | 30.85 (26–36) | |
| Flower: attitude of styles | erect | [semi-erect] |
| Flower: curvature of styles | straight | [strongly curved] |

-continued

TABLE OF CHARACTERISTICS

Horticultural terminology is used in accordance with revised UPOV guidelines for kiwi.

Characters of comparison cultivar 'Hayward' are noted opposite that character in [brackets] when significantly different.

'Hayward' plants were observed in a planting on the same orchard, but not the same plot.

All dimensions in millimeters unless otherwise stated, weights in grams.

| | Hort16A | Hayward |
|---|---|---|
| Flower: amount of hair on ovary | strongly expressed | |
| FRUIT (Measurements are from a 10 fruit sample) | | |
| Fruit: overall size | large 98.3 g (43–176 g) | |
| Fruit: length | 79.1 mm (76.0–84.2 mm) | |
| Fruit: width (max.) | 53.1 mm (55.4–48.1 mm) | |
| Fruit: width (min.) | 49.1 mm (47.0–51.2 mm) | |
| Fruit: core diameter (max.) | 13.1 mm (9.3–17 mm) | |
| Fruit: core diameter (min.) | 4.9 mm (4.1–6.1 mm) | |
| Fruit: locule number | 34.5 (26–37) | |
| Fruit: peduncle length | 48.3 mm (44.7–50.3 mm) | |
| Fruit: peduncle width | 3.57 mm (3.22–4.28 mm) | |
| Fruit: general shape | ovoid | [cylindrical] |
| Fruit: cross-section at median | elliptic | |
| Fruit: general shape of stylar end | protruding | [flat] |
| Fruit: shape of shoulder on stalk end | rounded | |
| Fruit: skin color at harvest (fruit still hard) | yellow-brown | [brown] |
| Fruit: skin color change during ripening | absent | |
| Fruit: skin color at maturity for consumption | yellow-brown | [brown] |
| Fruit: hairs | present | |
| Fruit: density of hairs | medium | |
| Fruit: type of hair | pubescent | [hirsute] |
| Fruit: hair length | short | [medium] |
| Fruit: concentration of hairs | uniform | |
| Fruit: adherence of hairs to skin (when rubbed) | weak | [strong] |
| Fruit: core diameter (at largest diameter) | small | [large] |
| Fruit: core shape (in cross section) | elliptical | |
| Fruit: core woody spike | present | |
| Fruit: prominence of core woody spike | weak | [medium] |
| Fruit: outer pericarp color at maturity for consumption | golden yellow | [green] |
| Fruit: inner pericarp color (locules) at maturity for consumption | brownish-yellow | [green] |
| Fruit: core color at maturity | white | [greenish white] |
| Fruit: sweetness (Brix level) at maturity for consumption | 15.6% (14.4–17.0%) | |
| Fruit: Vitamin C content | medium (125 mg/100 g fresh weight) | |
| Fruit: seed color at maturity | dark brown | |
| Fruit: seed color when dry | brown | |
| EVENTS (at Te Puke, New Zealand) | | |
| Time of vegetative budbreak | late August to first week of September | |
| Time of beginning of flowering | late October to first week of November | |

-continued

TABLE OF CHARACTERISTICS

Horticultural terminology is used in accordance with revised UPOV guidelines for kiwi.

Characters of comparison cultivar 'Hayward' are noted opposite that character in [brackets] when significantly different.

'Hayward' plants were observed in a planting on the same orchard, but not the same plot.

All dimensions in millimeters unless otherwise stated, weights in grams.

| | Hort16A | Hayward |
|---|---|---|
| Time of maturity for harvest (at 10.0% SSC) | first-second week of May | |

HORTICULTURAL CHARACTERISTICS

Details below relate to observations made on plants growing at Te Puke Research Centre, New Zealand. These plants were grafted on to *A. deliciosa* seedling rootstocks.

'Hort16A' vines can be grown on the same rootstocks as can 'Hayward'. Rootstocks currently being used in New Zealand include *A.deliciosa* seedlings, 'Hayward' rooted cuttings and Hortkiwi 'Kaimai'.

Cropping: young vines of 'Hort16A' carry higher yields than 'Hayward' when plants of equivalent ages are compared, although at maturity, yields are likely to be similar. The storage life of 'Hort16A' fruit is about 75% of that of 'Hayward' fruit under a coolstorage temperature of 0° C. 'Hort16A' fruit soften in coolstore more rapidly than 'Hayward' fruit initially, but will hold at a ready to eat firmness of about 1 kg for over two months after the initial softening period.

OTHER DATA

Fruit size: Data from a random harvest of 1940 fruit which were graded to measure fruit size in May 1995. Individual fruit weights collected electronically from the grader.

Mean fruit weight: 98.3 g.

*Minimum.*—43 g.

*Maximum.*—176 g.

Standard error of the mean (SEM): 0.574.

COLOR CHART RHS Colour Chart, the Royal Horticultural Society, London 1966.

| | | |
|---|---|---|
| Flesh Color at maturity: | | |
| Outer pericarp | | |
| Hort16A | 12C–12B | [Hayward 138B–138C] |
| Inner pericarp | | |
| Hort16A | 162A–162C | |
| Fruit core at harvest: | | |
| Hort16A | 159C | [Hayward 155A] |
| Seed color (in flesh): | 200A | |
| Seed color (dry seed): | 200D | |
| Fruit skin at maturity: | combination of | |
| Hort16A | 199A plus 161A | |
| Leaf color: mature leaf after petal fall | | |
| Upper side of leaf | | |
| Hort16A | 146A | [Hayward 147A] |
| Lower side of leaf | | |
| Hort16A | 147B | [Hayward 147C] |
| Flower petals: | | |
| main body of petal | 155D | |
| Plant stem: | | |
| exposed side | 200B–200C-165A | [Hayward 147C] |

We claim:

1. A new and distinct kiwi plant of the species *A. chinensis* substantially as described and illustrated, characterized by yellow flesh with a sweet, tropical taste, ovoid fruit shape with a protruding stylar end, and yellow brown skin with soft fine hairs.

* * * * *